(12) United States Patent
Hur et al.

(10) Patent No.: US 8,754,936 B2
(45) Date of Patent: Jun. 17, 2014

(54) THREE DIMENSIONAL SHAPE MEASUREMENT APPARATUS

(75) Inventors: Jung Hur, Bucheon-si (KR);
Moon-Young Jeon, Seoul (KR);
Hong-Min Kim, Seoul (KR); Sang-Kyu Yun, Chungju-si (KR); Jong-Kyu Hong, Gwangju-si (KR)

(73) Assignee: Koh Young Technology Inc., Seoul (KR)

( * ) Notice: Subject to any disclaimer, the term of this patent is extended or adjusted under 35 U.S.C. 154(b) by 396 days.

(21) Appl. No.: 12/828,615

(22) Filed: Jul. 1, 2010

(65) Prior Publication Data

US 2011/0001818 A1 Jan. 6, 2011

(30) Foreign Application Priority Data

Jul. 3, 2009 (KR) .................. 10-2009-0060865
Jan. 6, 2010 (KR) .................. 10-2010-0000721

(51) Int. Cl.
*H04N 7/18* (2006.01)
*G01B 9/02* (2006.01)
*G01B 11/14* (2006.01)
*G01B 11/24* (2006.01)
*G01B 11/30* (2006.01)

(52) U.S. Cl.
USPC ............ 348/87; 348/86; 356/450; 356/616; 356/618; 356/610; 356/604; 359/569

(58) Field of Classification Search
USPC .............. 348/86–87; 356/604–605, 450, 356/616–618
See application file for complete search history.

(56) References Cited

U.S. PATENT DOCUMENTS

| | | | | |
|---|---|---|---|---|
| 3,619,065 A | * | 11/1971 | Agnew | 356/604 |
| 5,461,455 A | * | 10/1995 | Coteus et al. | 355/43 |
| 6,239,909 B1 | * | 5/2001 | Hayashi et al. | 359/569 |
| 2008/0278729 A1 | * | 11/2008 | Kim | 356/450 |

FOREIGN PATENT DOCUMENTS

| | | |
|---|---|---|
| DE | 41 34 546 A1 | 4/1993 |
| DE | 44 16 108 A1 | 11/1995 |
| DE | 11 2004 000 267 T5 | 1/2007 |
| JP | 54-032346 | 3/1979 |
| JP | 07-019825 | 1/1995 |
| JP | 2002-257527 A | 9/2002 |
| JP | 2004-125652 A | 4/2004 |
| JP | 2005-106491 | 4/2005 |
| JP | 2005-135935 | 5/2005 |
| JP | 2006-516719 | 7/2006 |
| JP | 2007-163498 A | 6/2007 |
| JP | 2007-256278 | 10/2007 |
| JP | 2008-122361 A | 5/2008 |
| JP | 2008-281543 | 11/2008 |
| WO | 2004/070316 | 8/2004 |

* cited by examiner

*Primary Examiner* — Allen Wong
*Assistant Examiner* — Farhan Mahmud
(74) *Attorney, Agent, or Firm* — Kile Park Reed & Houtteman PLLC

(57) ABSTRACT

A three dimensional shape measurement apparatus includes an illumination section and a grating transfer unit. The illumination section includes a light source unit generating a light and a grating unit changing the light generated by the light source unit into a grating pattern light having a grating pattern. The illumination section illuminates the grating pattern light onto a measurement target in a predetermined direction. The grating transfer unit transfers the grating unit in a predetermined inclination direction with respect to an extension direction of the grating pattern and an arrangement direction of the grating pattern. Thus, manufacturing cost may be reduced, and the three dimensional shape measurement apparatus may be easily managed.

13 Claims, 13 Drawing Sheets

THREE DIMENSIONAL SHAPE MEASUREMENT APPARATUS

CROSS REFERENCE TO RELATED APPLICATION

This application claims priority from and the benefit of Korean Patent Applications No. 2009-60865 filed on Jul. 3, 2009, and No. 2010-721 filed on Jan. 6, 2010, which are hereby incorporated by reference for all purposes as if fully set forth herein.

BACKGROUND OF THE INVENTION

1. Field of the Invention

Exemplary embodiments of the present invention relate to a three dimensional shape measurement apparatus. More particularly, exemplary embodiments of the present invention relate to a three dimensional shape measurement apparatus measuring a three dimensional shape by illuminating a grating pattern light.

2. Discussion of the Background

Generally, a three dimensional shape measurement apparatus illuminates a grating pattern light onto a measurement target and photographs a reflection image by the grating pattern light to measure a three dimensional shape of the measurement target. The three dimensional shape measurement apparatus typically includes a stage, a camera, an illumination unit, a central processing section, etc.

Typically, measuring a three dimensional shape of a measurement target by using the three dimensional shape measurement apparatus is performed as follows.

First, a grating pattern light from the illumination unit is incident onto a measurement target disposed on the stage. The grating pattern light is incident onto the measurement target while moving N times. Thereafter, the camera acquires N pattern images of the measurement target by detecting the grating pattern light reflected by the measurement target. Then, the central processing section calculates height for each location from N pattern images by using an N-bucket algorithm. The three dimensional shape of the measurement target is measured by using the calculated height for each location.

A conventional three dimensional shape measurement apparatus illuminates grating pattern lights in a plurality of directions to precisely measure a three dimensional shape. The three dimensional shape can be measured only when transferring a grating pattern for generating the grating pattern light by N times in a direction parallel with illumination direction of the grating pattern light when viewed in a plan view. Thus, a conventional transfer direction of the grating pattern is substantially in parallel with an arrangement direction of the grating pattern, i.e., substantially perpendicular to an extension direction of the grating pattern. Accordingly, when viewed in a front view, a grating unit disposed at a left side has been transferred from lower left to upper right, and a grating unit disposed at a right side has been transferred from lower right to upper left.

Since it is difficult that transferring two grating units by using one grating transfer unit is directly performed, conventionally, independent grating transfer units has been employed corresponding to a plurality of directions, or the transfer direction has been obtained by using a predetermined optical system such as a reflection minor.

However, when the independent grating transfer units and the optical system are employed for grating pattern light, manufacturing cost is increased for installing the plurality of grating transfer units or the optical system, and it is required to independently control and manage the grating transfer units or managing the optical system.

SUMMARY OF THE INVENTION

Exemplary embodiments of the present invention provide a three dimensional shape measurement apparatus capable of reducing manufacturing cost and being easily managed.

Exemplary embodiments of the present invention also provide a board inspection apparatus capable of reducing manufacturing cost, making an illumination section small, enhancing inspection precision and simplifying control.

Exemplary embodiments of the present invention also provide a board inspection method of inspecting a board by using the board inspection apparatus.

Additional features of the invention will be set forth in the description which follows, and in part will be apparent from the description, or may be learned by practice of the invention.

An exemplary embodiment of the present invention discloses a three dimensional shape measurement apparatus including a first illumination section and a grating transfer unit. The first illumination section includes a first light source unit generating a light and a first grating unit changing the light generated by the first light source unit into a first grating pattern light having a first grating pattern. The first illumination section illuminates the first grating pattern light onto a measurement target in a first direction. The grating transfer unit transfers the first grating unit in a first inclination direction with respect to an extension direction of the first grating pattern and an arrangement direction of the first grating pattern.

The three dimensional shape measurement apparatus may further include a second illumination section including a second light source unit generating a light and a second grating unit changing the light generated by the second light source unit into a second grating pattern light having a second grating pattern. The second illumination section illuminates the second grating pattern light onto the measurement target in a second direction different from the first direction. The grating transfer unit simultaneously transfers the first grating unit and the second grating unit in a grating transfer direction, and the second grating unit is transferred in a second inclination direction with respect to an extension direction of the second grating pattern and an arrangement direction of the second grating pattern.

Each of the first and second grating units may include an inclination angle control part controlling an inclination angle of the first and second inclination directions, respectively, and/or the first and second grating units may be replaceable to control the inclination angle.

The first grating pattern of the first grating unit and the second grating pattern of the second grating unit may have an extension direction corresponding to one of a direction substantially in parallel with each other and a direction substantially symmetrical to each other when viewed in a plan view.

The first grating pattern light and the second grating pattern light may be directly illuminated onto the measurement target.

A first equivalent grating transfer direction of the first grating unit and a second equivalent grating transfer direction of the second grating unit may be different from the grating transfer direction.

When an angle between the arrangement direction of the first grating pattern and the grating transfer direction is $\theta$, and a transfer distance of the first grating transfer unit is d, an equivalent grating transfer distance may be $d/\tan\theta$.

Another exemplary embodiment of the present invention discloses a three dimensional shape measurement apparatus including a first illumination section, a second illumination section and a grating transfer unit. The first illumination section includes a first light source unit generating a light and a first grating unit changing the light generated by the first light source unit into a first grating pattern light having a first grating pattern. The first illumination section illuminates the first grating pattern light onto a measurement target in a first direction. The second illumination section includes a second light source unit generating a light and a second grating unit changing the light generated by the second light source unit into a second grating pattern light having a second grating pattern. The second illumination section illuminates the second grating pattern light onto the measurement target in a second direction different from the first direction. The grating transfer unit simultaneously transfers the first grating unit and second grating unit that are respectively disposed on two inclination faces so that the grating transfer unit is moved on the two inclination faces. The two inclination faces are adjacent to each other to define an edge of an N-angular pyramid.

The grating transfer unit may move along the edge defined by the two inclination faces on which the first grating unit and the second grating unit are disposed.

Still another exemplary embodiment of the present invention discloses a board inspection apparatus. The board inspection apparatus includes a plurality of illumination sections each of which includes a light source unit generating a light, a grating unit changing the light generated by the first light source unit into a grating pattern light, and a projecting lens projecting the grating pattern light, a light path changing section providing the grating pattern light passing through the projecting lens to a measurement target, a grating transfer unit simultaneously transferring the grating units of the illumination sections by a predetermined number of times, an image photographing module photographing images by using the grating pattern lights reflected by the measurement target, and a control section inspecting the measurement target by using the photographed images by the photographing module. The grating units are disposed on a same plane and simultaneously transferred on the same plane by the grating transfer unit.

The light path changing section may include a plurality of first reflecting mirrors reflecting the grating pattern light passing through the projecting lens and a plurality of second reflecting minors reflecting the grating pattern light reflected by the first reflecting minor and providing the reflected grating pattern light to the measurement target. When an angle between the grating plane and a reference surface of the projecting lens is defined as a grating angle ($\theta$grat), an angle between a normal line of the first reflecting mirror and the grating plane RP is defined as a first minor angle ($\theta$mir1), an angle between a normal line of the second reflecting minor and the grating plane is defined as a second mirror angle ($\theta$mir2), and an angle between an incident light that is reflected by the first and second reflecting minors and incident onto the inspection board and the normal line of the grating plane is defined as a projecting angle ($\theta$proj), the projecting lens and the first and second reflecting minors may have a relation of an equation, "$\theta$mir1−17$\theta$mir2=($\theta$grat+$\theta$proj)/2".

The grating transfer unit may simultaneously transfer the grating units in a direction different from grating pattern directions of the grating units.

The reference surfaces of the projecting lenses may form a predetermined angle with respect to the grating plane.

Still another exemplary embodiment of the present invention discloses a board inspection method. The board inspection method includes simultaneously transferring grating units along a same plane by a predetermined pitch in a grating transfer direction different from grating pattern directions of the grating units disposed on the same plane, providing grating pattern light passing through the grating units to the inspection board through a light path changing section, and receiving the grating pattern light reflected by the inspection board to photograph an image.

According to the present invention, a grating transfer unit transfers a grating unit in a direction inclined with respect to an arrangement direction and an extension direction of a grating pattern, and thus at least two grating units may be transferred by using one grating transfer unit even though not employing an optical system such as an independent light path changing means, to thereby reduce manufacturing cost and easily control and manage an apparatus.

In addition, an inclination angle between the arrangement direction of the grating pattern and the transfer direction of the grating transfer unit is properly controlled to obtain greater transfer effect or precise transfer effect in comparison with a real transfer.

In addition, according to moving grating units disposed on the same grating plane by using one grating transfer unit, the number of the grating transfer unit may be reduced, manufacturing cost of a board inspection apparatus may be reduced, and each size of illumination sections may be reduced.

In addition, reduction of inspection precision due to transfer difference between many conventional grating transfer units may be prevented, and control complexity due to independently operating the grating transfer units may be reduced.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
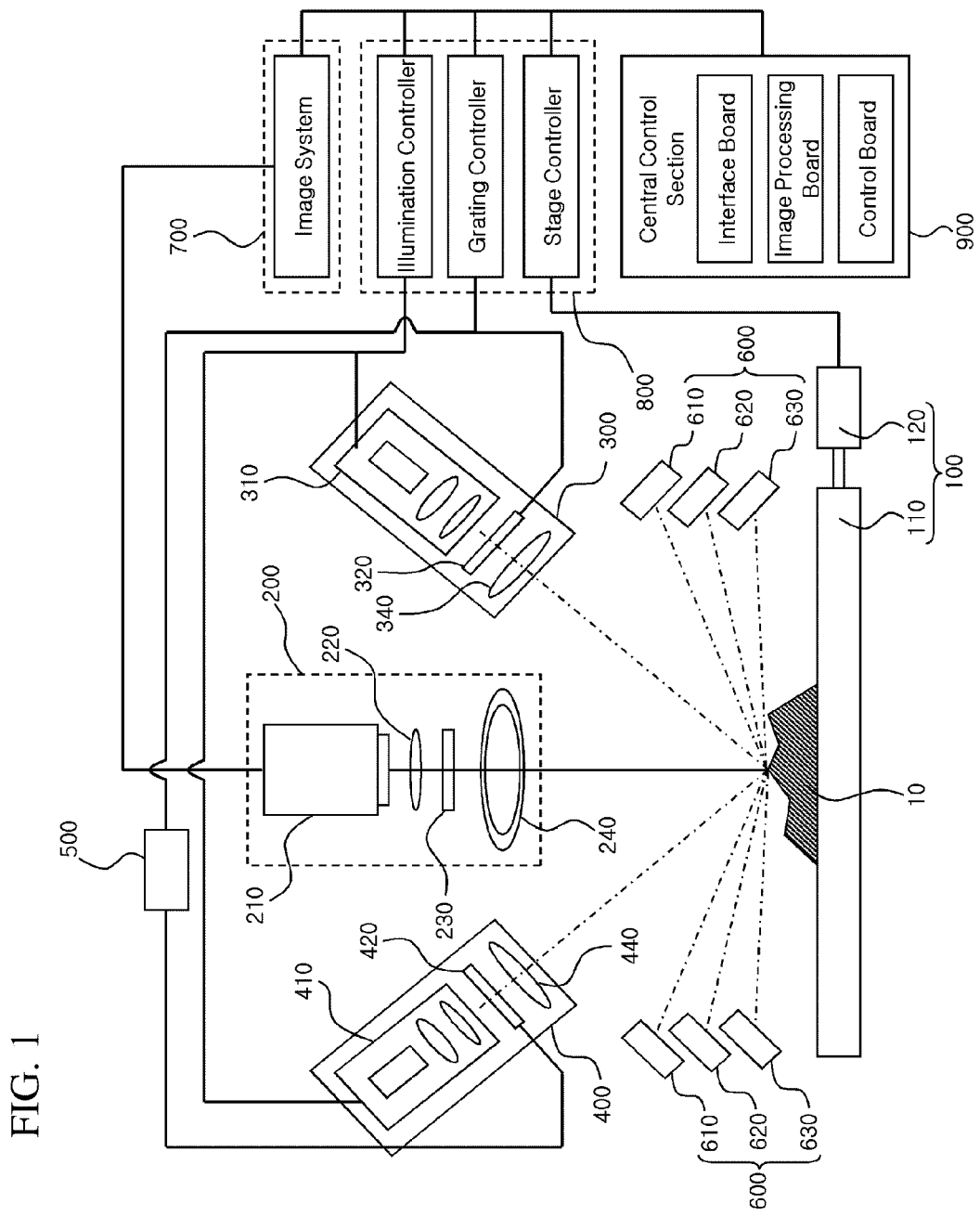
FIG. 1 is a schematic view illustrating a three dimensional shape measurement apparatus used to a method of measuring a three dimensional shape according to an exemplary embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

FIG. 1 is a schematic view illustrating a three dimensional shape measurement apparatus used to a method of measuring a three dimensional shape according to an exemplary embodiment of the present invention.

Referring to FIG. 1, a three dimensional shape measurement apparatus used to a method of measuring a three dimensional shape according to an exemplary embodiment of the present invention may include a measurement stage section 100, an image photographing section 200, a first illumination unit including first and second illumination sections 300 and 400, a grating transfer unit 700, a second illumination unit 600, an image acquiring section 700, a module control section 800 and a central control section 900.

The measurement stage section 100 may include a stage 110 supporting a measurement target 10 and a stage transfer unit 120 transferring the stage 110. In an exemplary embodiment, according as the measurement target 10 moves with respect to the image photographing section 200 and the first and second illumination sections 300 and 400 by the stage 110, a measurement location may be changed in the measurement target 10.

The image photographing section 200 is disposed over the stage 110 to receive light reflected by the measurement target 10 and measure an image of the measurement target 10. That is, the image photographing section 200 receives the light that exits the first and second illumination sections 300 and 400 and is reflected by the measurement target 10, and photographs a plan image of the measurement target 10.

The image photographing section 200 may include a camera 210, an imaging lens 220, a filter 230 and a lamp 240. The camera 210 receives the light reflected by the measurement target 10 and photographs the plan image of the measurement target 10. The camera 210 may include, for example, one of a CCD camera and a CMOS camera. The imaging lens 220 is disposed under the camera 210 to image the light reflected by the measurement target 10 on the camera 210. The filter 230 is disposed under the imaging lens 220 to filter the light reflected by the measurement target 10 and provide the filtered light to the imaging lens 220. The filter 230 may include, for example, one of a frequency filter, a color filter and a light intensity control filter. The lamp 240 may be disposed under the filter 230 in a circular shape to provide the light to the measurement target 10, so as to photograph a particular image such as a two-dimensional shape of the measurement target 10.

The first illumination section 300 may be disposed, for example, at a right side of the image photographing section 200 to be inclined with respect to the stage 110 supporting the measurement target 10. The first illumination section 300 illuminates a first grating pattern light onto the measurement target 10 in a first direction.

The first illumination section 300 may include a first light source unit 310, a first grating unit 320 and a first condensing lens 340. The first light source unit 310 may include a light source and at least one lens to generate light, and the first grating unit 320 is disposed under the first light source unit 310 to change the light generated by the first light source unit 310 into a first grating pattern light having a first grating pattern. The first condensing lens 340 is disposed under the first grating unit 320 to condense the first grating pattern light exiting the first grating unit 320 on the measurement target 10.

For example, the second illumination section 400 may be disposed at a left side of the image photographing section 200 to be inclined with respect to the stage 110 supporting the measurement target 10. The second illumination section 400 illuminates a second grating pattern light onto the measurement target 10 in a second direction different from the first direction.

The second illumination section 400 may include a second light source unit 410, a second grating unit 420 and a second condensing lens 440. The second light source unit 410 may include a light source and at least one lens to generate light, and the second grating unit 420 is disposed under the second light source unit 410 to change the light generated by the second light source unit 410 into a second grating pattern light having a second grating pattern. The second condensing lens 440 is disposed under the second grating unit 420 to condense the second grating pattern light exiting the second grating unit 420 on the measurement target 10. The second grating unit 420 is substantially the same as the first grating unit 320 except for the first grating pattern, and the second grating pattern may be also substantially the same as the first grating pattern.

When sequentially moving the first grating unit 320 by N times and illuminating N first grating pattern lights onto the measurement target 10 in the first illumination section 300, the image photographing section 200 may sequentially receive the N first grating pattern lights reflected by the measurement target 10 and photograph N first pattern images. In addition, when sequentially moving the second grating unit 420 by N times and illuminating N second grating pattern lights onto the measurement target 10 in the second illumination section 400, the image photographing section 200 may sequentially receive the N second grating pattern lights reflected by the measurement target 10 and photograph N second pattern images. The 'N' is a natural number, and for example may be four.

In an exemplary embodiment, the first and second illumination sections 300 and 400 are described as an illumination apparatus generating the first and second grating pattern lights. Alternatively, the illumination section may be more than or equal to three. In other words, the grating pattern light may be illuminated onto the measurement target 10 in various directions, and various pattern images may be photographed. For example, when three illumination sections are disposed in an equilateral triangle form with the image photographing section 200 being the center of the equilateral triangle form, three grating pattern lights may be illuminated onto the measurement target 10 in different directions. For example, when four illumination sections are disposed in a square form with the image photographing section 200 being the center of the square form, four grating pattern lights may be illuminated onto the measurement target 10 in different directions. In addition, the first illumination unit may include eight illumination sections, and grating pattern lights may be illuminated onto the measurement target 10 in eight directions to photograph an image.

The grating transfer unit 500 transfers the first grating unit 320 in a direction inclined with respect to an arrangement direction of the first grating pattern and an extension direction of the first grating pattern, and transfers the second grating unit 420 in a direction inclined with respect to an arrangement direction of the second grating pattern and an extension direction of the second grating pattern. The grating transfer unit 500 may simultaneously transfers the first grating unit 320 and the second grating unit 420. A detail transfer method of the grating transfer unit 500 will be described later.

The second illumination unit 600 illuminates light for acquiring a two dimensional image of the measurement target 10 onto the measurement target 10. In an exemplary embodiment, the second illumination unit 600 may include a red illumination 610, a green illumination 620, and a blue illumination 630. For example, the red illumination 610, the green illumination 620, and the blue illumination 630 may be disposed in a circular shape over the measurement target 10 to illuminate a red light, a green light and a blue light, respectively, and may be disposed at different heights as shown in FIG. 1.

The image acquiring section 700 is electrically connected to the camera 210 of the image photographing section 200 to acquire the pattern images according to the first illumination unit from the camera 210 and store the acquired pattern images. In addition, the image acquiring section 700 acquires the two dimensional images according to the second illumination unit from the camera 210 and store the acquired two dimensional images. For example, the image acquiring section 700 may include an image system that receives the N first pattern images and the N second pattern images photographed in the camera 210 and stores the images.

The module control section 800 is electrically connected to the measurement stage section 100, the image photographing section 200, the first illumination section 300 and the second illumination section 400, to control the measurement stage section 100, the image photographing section 200, the first illumination section 300 and the second illumination section 400. The module control section 800 may include, for example, an illumination controller, a grating controller and a stage controller. The illumination controller controls the first and second light source units 310 and 410 to generate light, and the grating controller controls the grating transfer unit 500 to move the first and second grating units 320 and 420. The stage controller controls the stage transfer unit 120 to move the stage 110 in an up-and-down motion and a left-and-right motion.

The central control section 900 is electrically connected to the image acquiring section 700 and the module control section 800 to control the image acquiring section 700 and the module control section 800. Particularly, the central control section 900 receives the N first pattern images and the N second pattern images from the image system of the image acquiring section 700 to process the images, so that three dimensional shape of the measurement target may be measured. In addition, the central control section 900 may control an illumination controller, a grating controller and a stage controller of the module control section 800. Thus, the central control section may include an image processing board, a control board and an interface board.

Figure 2:
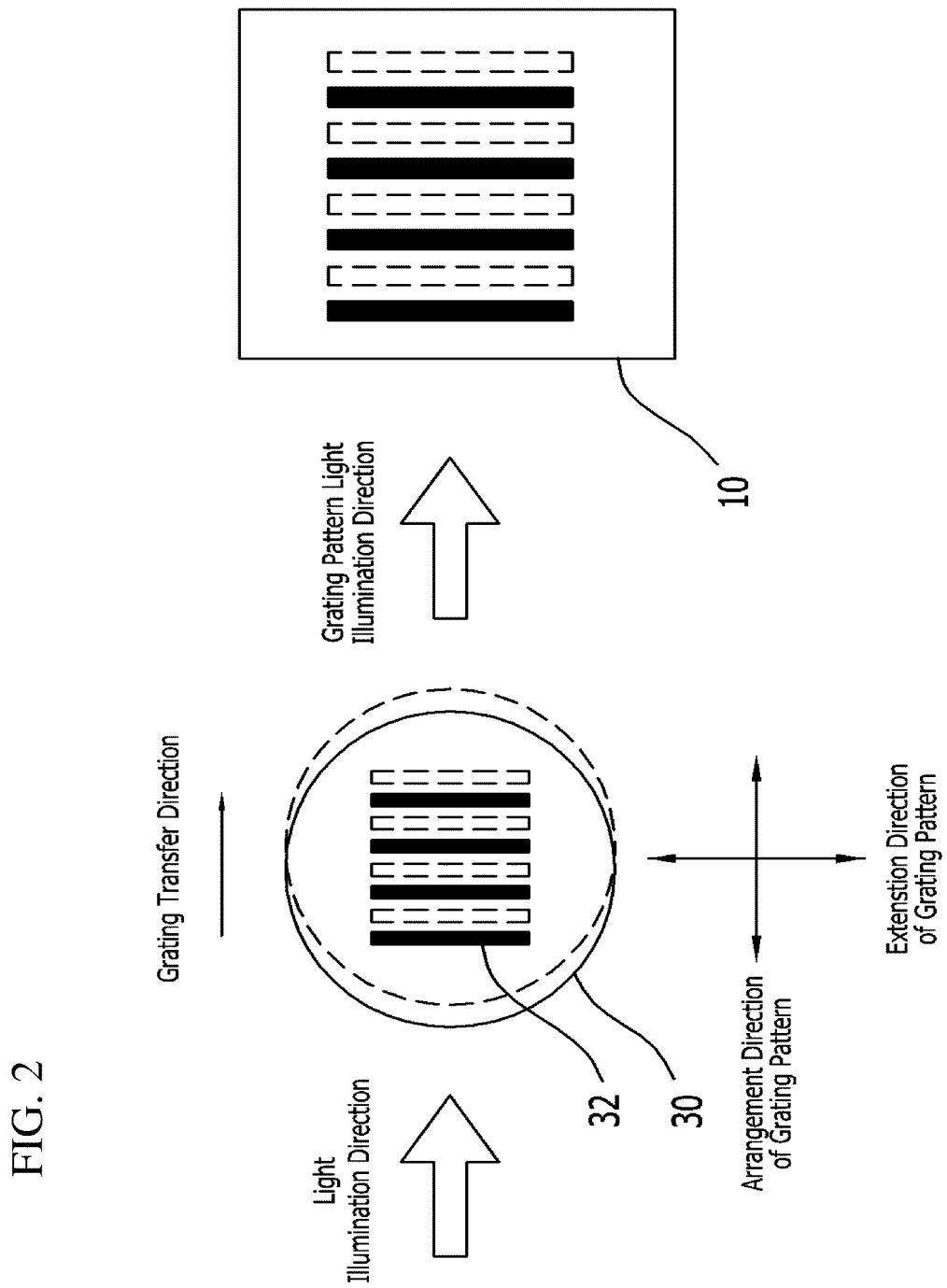
FIGS. 2 and 3 are schematic views illustrating a transfer direction of a conventional grating unit.
Figure 3:
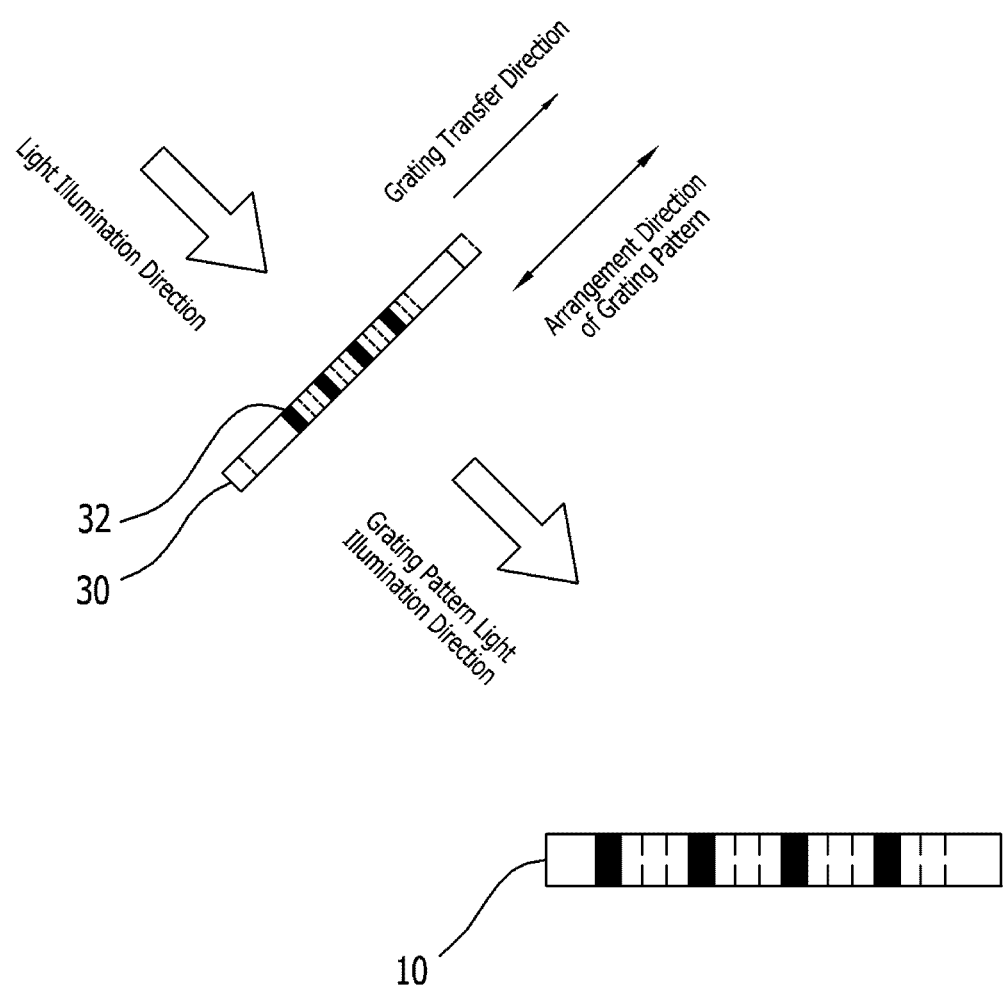

FIGS. 2 and 3 are schematic views illustrating a transfer direction of a conventional grating unit. FIG. 2 is a schematic view when a conventional three dimensional shape measurement apparatus is viewed in a plan view. FIG. 3 is a schematic view when the conventional three dimensional shape measurement apparatus is viewed in a front view.

Referring to FIGS. 2 and 3, for example, when a grating unit 30 is disposed at a left side of a measurement target 10 and transferred from lower left to upper right, in order to move the grating unit 30, a grating transfer unit (not shown) is required to transfer the grating unit 30 from lower left to upper right.

A light generated at an upper left passes through the grating pattern 32 to form a grating pattern light, and the grating pattern light is illuminated to lower right. When the grating pattern 32 is viewed in a plan view from upper portion, the grating pattern 32 is transferred from left to right as shown in FIG. 2, the transfer direction is substantially the same as or substantially in parallel with an illumination direction when the grating pattern light is viewed in a plan view from upper portion. Particularly, the grating pattern 32 is transferred by N times in a direction substantially in parallel with an arrangement direction of the grating pattern 32, i.e., a direction substantially perpendicular to an extension direction of the grating pattern 32 to detect a reflection image according to the grating pattern light and measure a three dimensional shape of the measurement target 10.

Accordingly, when grating pattern lights are illuminated onto the measurement target 10 in at least two directions, the grating unit 30 is transferred from lower left to upper right, and another grating unit (not shown) disposed at a right side of the measurement target 10 is required to be transferred from lower right to upper left or from upper left to lower right.

As a result, the grating unit 30 disposed at a left side of the measurement target 10 and another grating unit disposed at a right side of the measurement target 10 cannot be transferred in substantially the same direction. Thus, independent grating transfer units need to be employed corresponding to the left grating unit 30 and the right grating unit, or an additional optical system such as a reflection minor need to be employed to obtain the transfer directions.

Figure 4:
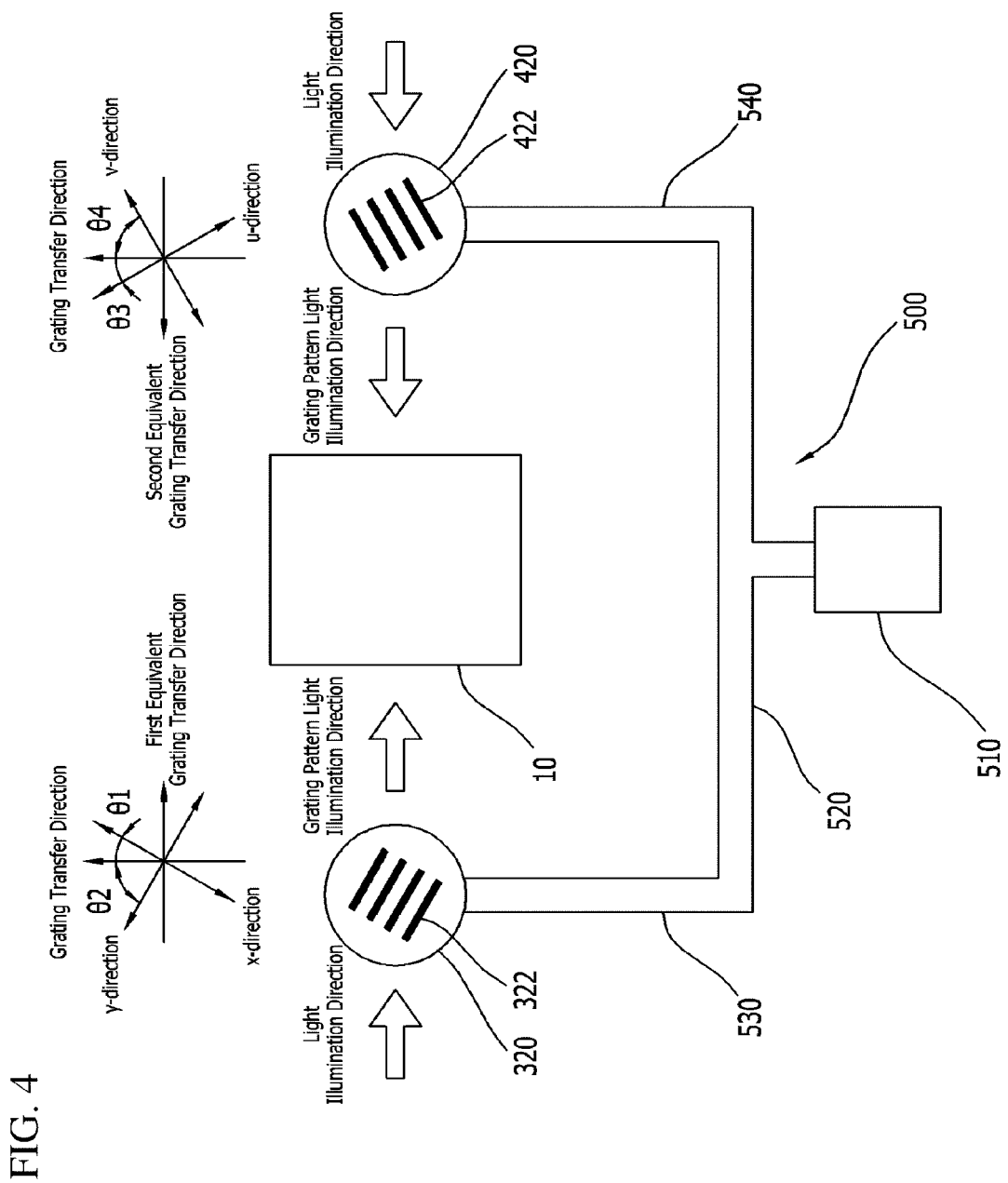
FIG. 4 is a schematic view illustrating an example of a detailed transfer method of the grating transfer unit in FIG. 1.
Figure 5:
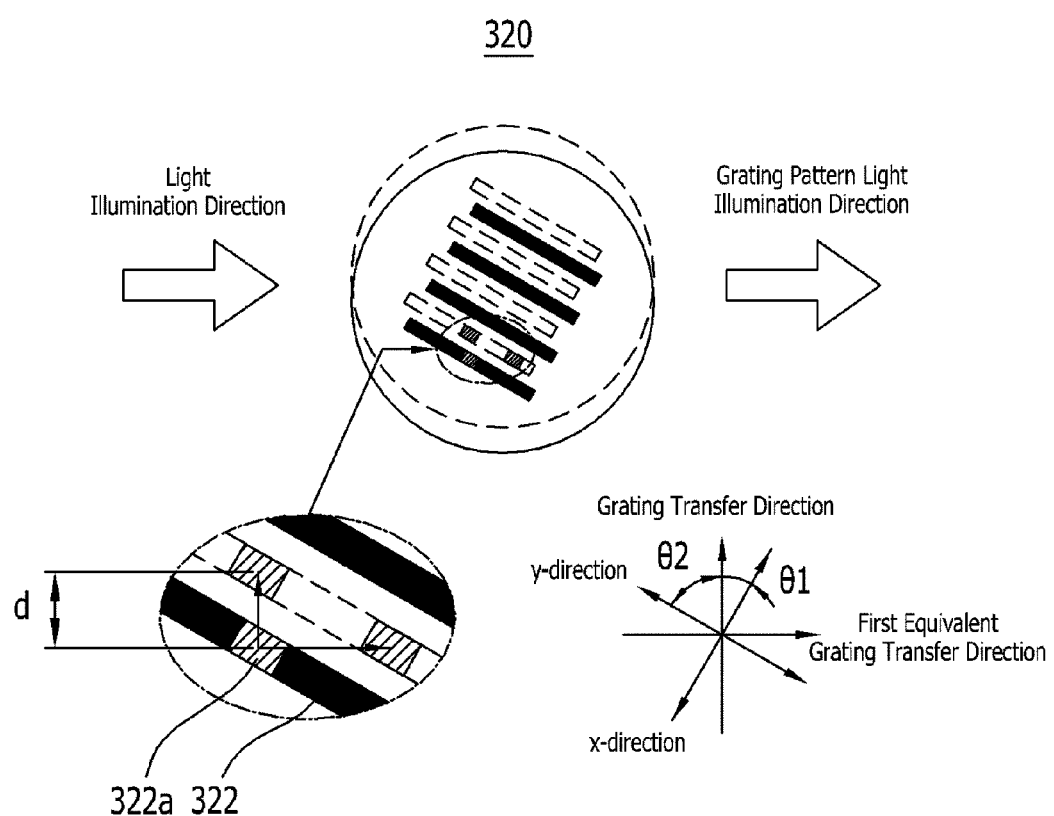
FIG. 5 is a schematic view illustrating the first grating unit in FIG. 4.
Figure 6:
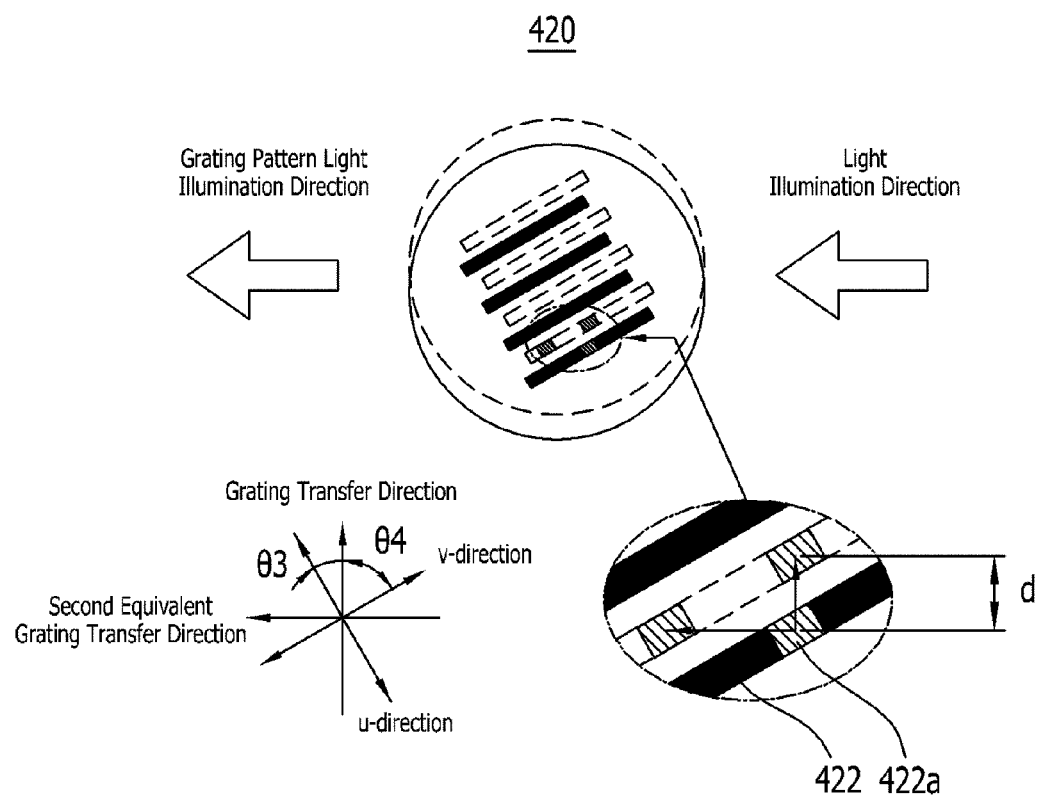
FIG. 6 is a schematic view illustrating the second grating unit in FIG. 4.

FIG. 4 is a schematic view illustrating an example of a detailed transfer method of the grating transfer unit in FIG. 1. FIG. 5 is a schematic view illustrating the first grating unit in FIG. 4. FIG. 6 is a schematic view illustrating the second grating unit in FIG. 4. FIGS. 4 to 6 are schematic views when the three dimensional shape measurement apparatus in FIG. 1 is viewed in a plan view.

Referring to FIGS. 4 to 6, the grating transfer unit 500 includes a transfer unit 510, a connection portion 520, a first grating connection portion 530 and a second grating connection portion 540.

The transfer unit 510 may include, for example, one of a piezoelectric (PZT) transfer unit and a fine linear transfer unit.

The transfer unit 510 is connected to the first grating connection portion 530 and the second grating connection portion 540 via the connection portion 520. The transfer unit 510 is connected to the first grating unit 320 and the second grating unit 420 by the first grating connection portion 530 and the second grating connection portion 540, respectively, to transfer the first grating unit 320 and the second grating unit 420.

Particularly, when viewed in a plan view from upper portion, the grating transfer unit 500 transfers the first grating unit 320 in a direction that is inclined by a first angle $\theta 1$ with respect to an x direction corresponding to an arrangement direction of the first grating pattern 322 and is inclined by a second angle $\theta 2$ with respect to a y direction corresponding to an extension direction of the first grating pattern 322. In addition, the grating transfer unit 500 transfers the second grating unit 420 in a direction that is inclined by a third angle $\theta 3$ with respect to a u direction corresponding to an arrangement direction of the second grating pattern 422 and is inclined by a fourth angle $\theta 4$ with respect to a v direction corresponding to an extension direction of the second grating pattern 422.

By the above-described transfer of the grating transfer unit 500, as shown in FIG. 5, any one material point 322a of the first grating pattern 322 of the first grating unit 320 is transferred in the grating transfer direction. However, it may be regarded that the material point 322a is transferred in a first equivalent grating transfer direction shown in FIG. 5, and thus it may be regarded that the first grating pattern 322 is transferred in the first equivalent grating transfer direction by the above-described transfer of the grating transfer unit 500. Hence, although a real transfer of the material point 322a is performed in the grating transfer direction, it may be regarded that the material point 322a is transferred in the first equivalent grating transfer direction.

When viewed in a plan view, while the grating transfer unit 500 is transferred by distance 'd', the first grating pattern 322 may be equivalently transferred by d/tan $\theta 1$=dtan $\theta 2$. Thus, for example, when the first angle $\theta 1$ is below 45 degrees and the second angle $\theta 2$ is above 45 degrees, greater transfer effect may be obtained in comparison with a real transfer of the grating transfer unit 500. In addition, for example, when the first angle $\theta 1$ is above 45 degrees and the second angle $\theta 2$ is below 45 degrees, precise transfer effect may be obtained in comparison with a real transfer of the grating transfer unit 500.

For example, the grating transfer unit 500 may transfer the first grating unit 320 in a direction inclined by about 10 degrees to about 80 degrees with respect to at least one of the x direction and the y direction. When the first angle $\theta 1$ is 10 degrees and the second angle $\theta 2$ is 80 degrees, distance of the equivalent transfer is about 5.67d, and thus greater transfer effect may be obtained in comparison with the real transfer. In addition, when the first angle $\theta 1$ is 80 degrees and the second angle $\theta 2$ is 10 degrees, distance of the equivalent transfer is about 0.18d, and thus more precise transfer effect of above five times may be obtained in comparison with the real transfer.

In an exemplary embodiment, the first grating unit 320 may include an inclination angle control part (not shown) controlling the inclination angle by controlling the arrangement direction of the first grating pattern 322 and the extension direction of the first grating pattern 322. Alternatively, the first grating unit 320 may be replaceable to control the inclination angle.

By the above-described transfer of the grating transfer unit 500, similarly to FIG. 5, although any one material point 422a of the second grating pattern 422 of the second grating unit 420 is transferred in the grating transfer direction, it may be regarded that the material point 422a is transferred in a second equivalent grating transfer direction shown in FIG. 6, opposite to the first equivalent grating transfer direction. Thus, although a real transfer of the second grating pattern 422 of the second grating unit 420 is performed in the grating transfer direction, it may be regarded that the second grating pattern 422 of the second grating unit 420 is transferred in the second equivalent grating transfer direction.

In an exemplary embodiment, the first grating unit 320 and the second grating unit 420 may be disposed at both sides of the measurement target 10, respectively, which is between the first grating unit 320 and the second grating unit 420. As shown in FIG. 4, the first grating pattern 322 of the first grating unit 320 and the second grating pattern 422 of the second grating unit 420 may be substantially symmetrical with respect to the measurement target 10 when viewed in a plan view. The third angle θ3 and the fourth angle θ4 are substantially the same as the first angle θ1 and the second angle θ2, respectively, and the u direction and the v direction are substantially symmetrical to the x direction and the y direction, respectively, with respect to the measurement target 10.

Alternatively, the first grating pattern 322 of the first grating unit 320 and the second grating pattern 422 of the second grating unit 420 may not be substantially symmetrical to each other with respect to the measurement target 10 when viewed in a plan view.

In FIG. 4, the first grating unit 320 of the first illumination section 300 and the second grating unit 420 of the second illumination section 400 are simultaneously transferred in substantially the same direction by the grating transfer unit 500. Thus, cost may be reduced and management and control is more effective in comparison with the case that independent grating transfer units are employed in order to transfer the first and second grating units 320 and 420.

Meanwhile, the first grating pattern light and the second grating pattern light are illuminated directly onto the measurement target without passing through a light path changing means, for example such as a mirror. In this case, installation cost of a separate light path changing means may be reduced.

Figure 7:
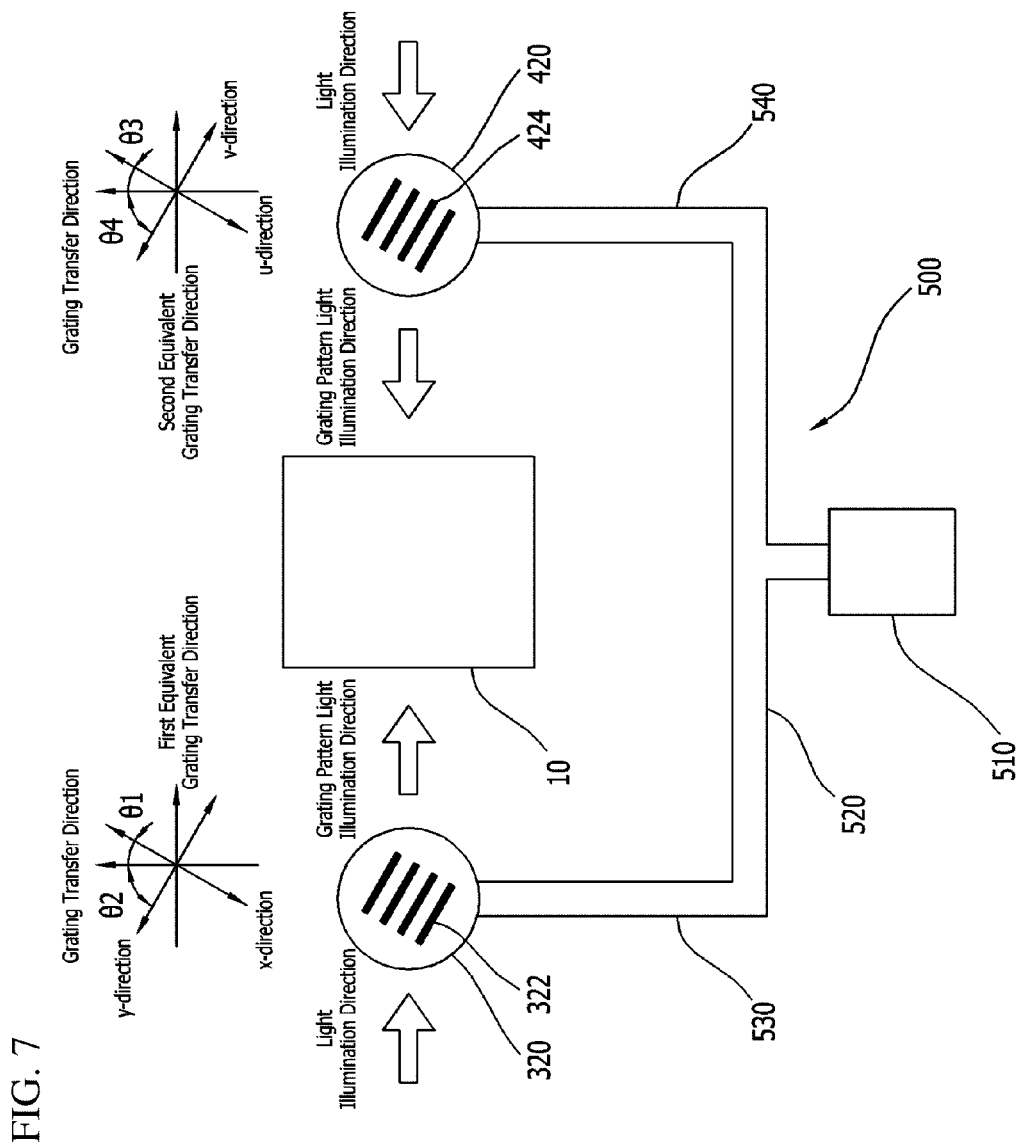
FIG. 7 is a schematic view illustrating another example of a detailed transfer method of the grating transfer unit in FIG. 1.

FIG. 7 is a schematic view illustrating another example of a detailed transfer method of the grating transfer unit in FIG. 1. The transfer method in FIG. 7 is substantially the same as the transfer method in FIG. 4 except for the transfer according to the second grating pattern 424 of the second grating unit 420, and thus any further description will be omitted.

Referring to FIG. 7, the first grating unit 320 and the second grating unit 420 may be disposed at both sides of the measurement target 10, respectively, which is between the first grating unit 320 and the second grating unit 420. As shown in FIG. 7, the first grating pattern 322 of the first grating unit 320 and the second grating pattern 424 of the second grating unit 420 may have an extension direction substantially in parallel with each other and an arrangement direction substantially in parallel with each other when viewed in a plan view.

The third angle θ3 and the fourth angle θ4 are substantially the same as the first angle θ1 and the second angle θ2, respectively, and the u direction and the v direction are substantially in parallel with the x direction and the y direction, respectively. In addition, in case that the grating transfer unit 500 transfers the first and second grating units 320 and 420 in the grating transfer direction, a first equivalent transfer direction of the first grating unit 320 and a second equivalent transfer direction of the second grating unit 420 are substantially the same.

The grating transfer unit 500 may move along an edge of a polyhedron. The first grating unit 320 and the second grating unit 420 are disposed on two adjacent inclination faces defining the edge, respectively, and may move on the two inclination faces, respectively. In this case, the three dimensional shape measurement apparatus may include at least one additional illumination section, in addition to the first and second illumination sections 300 and 400 illustrated in FIG. 1.

For example, in case that the three dimensional shape measurement apparatus in FIG. 1 includes N (greater than or equal to three) illumination sections, and grating pattern lights are illuminated onto the measurement target in N directions, the three dimensional shape measurement apparatus may include N grating units illuminating the N grating pattern lights. In this case, the grating transfer unit may transfer grating units corresponding to two adjacent directions.

In other words, the N grating units are respectively disposed on N inclination faces defining an N-angular pyramid, and the grating transfer unit moves along any one edge of the N-angular pyramid. The first and second grating units may be respectively disposed on a first inclination face and a second inclination face, which are adjacent to each other to define the edge, among the N inclination faces, and may move on the first and second inclination faces, respectively, according to movement of the grating transfer unit.

The N may be multiple of two. In other words, the N is expressed as N=2K (K is a natural number greater than or equal to two), and the three dimensional shape measurement apparatus may include K grating transfer units that is disposed between two adjacent grating units to transfer the two adjacent grating units. The K grating transfer units may be sequentially disposed every other edge among N edges of the N-angular pyramid.

Hereinafter, an example of the transfer method of the grating transfer unit will be described in detail with reference to the accompanying drawings.

Figure 8:
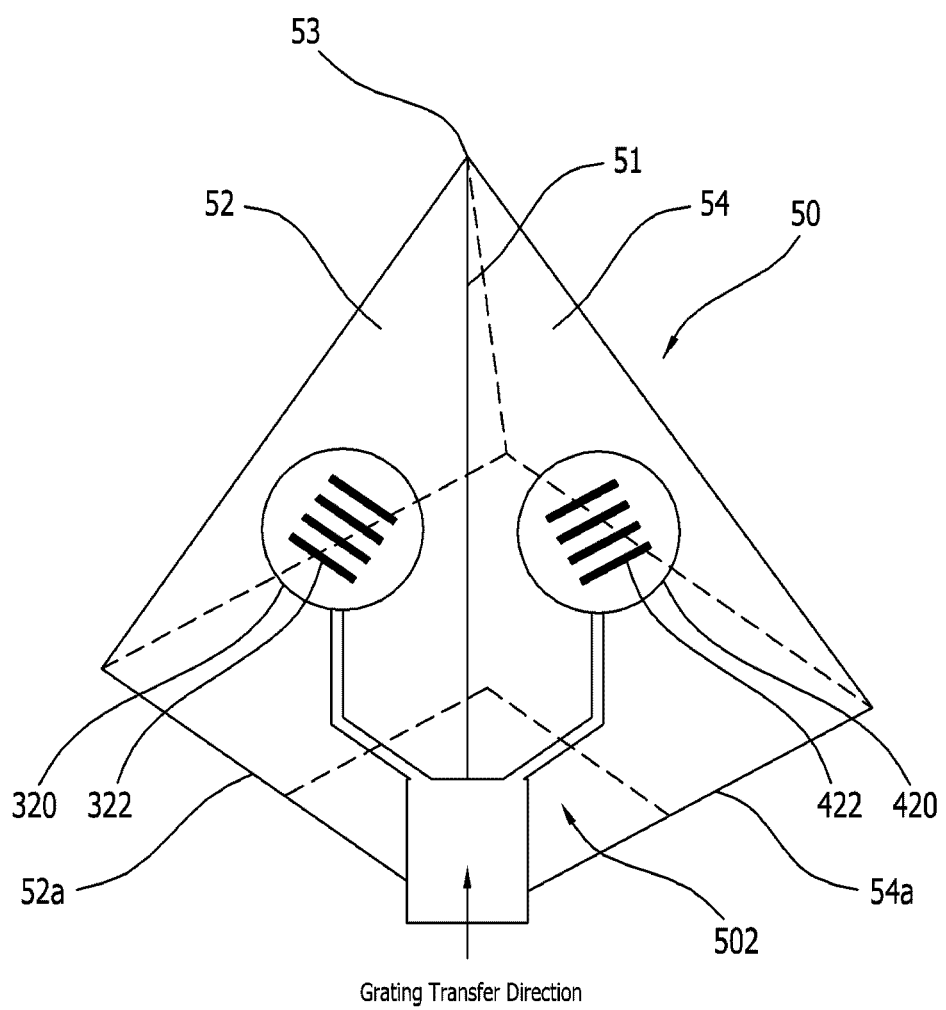
FIG. 8 is a schematic view illustrating an example of a detailed transfer method of a grating transfer unit according to another exemplary embodiment of the present invention.

FIG. 8 is a schematic view illustrating an example of a detailed transfer method of a grating transfer unit according to another exemplary embodiment of the present invention.

Referring to FIG. 8, for example, in case that the three dimensional shape measurement apparatus illustrated in FIG. 1 includes four illumination sections and grating pattern lights are illuminated in four directions, a grating transfer unit 502 transfers grating units 320 and 420 corresponding to two adjacent directions among the four directions.

For example, the grating transfer unit 502 may move along any one edge 51 of a quadrangular pyramid 50, and the first grating unit 320 and the second grating unit 420 are respectively disposed on adjacent first and second inclination faces 52 and 54 defining the edge 51 to move on the first and second inclination faces 52 and 54.

In the case of the above transfer, the grating transfer unit 502 moves toward a vertex 53 of the quadrangular pyramid 50, and the first and second grating units 320 and 420 are transferred to deviate from a direction toward the vertex 53 of the quadrangular pyramid 50. Thus, for example, in case that first and second grating patterns 322 and 422 are substantially parallel with first and second bottom sides 52a and 54a of the first and second inclination faces 52 and 54 on which the first and second grating units 320 and 420 are respectively disposed, the first and second grating units 320 and 420 are transferred in a direction inclined by a predetermined inclination angle with respect to an arrangement direction and an extension direction of the first and second grating patterns 322 and 422.

As a result of the above transfer method, the same effect as the transfer effect described in FIGS. 2 through 7 may be obtained.

Figure 9:
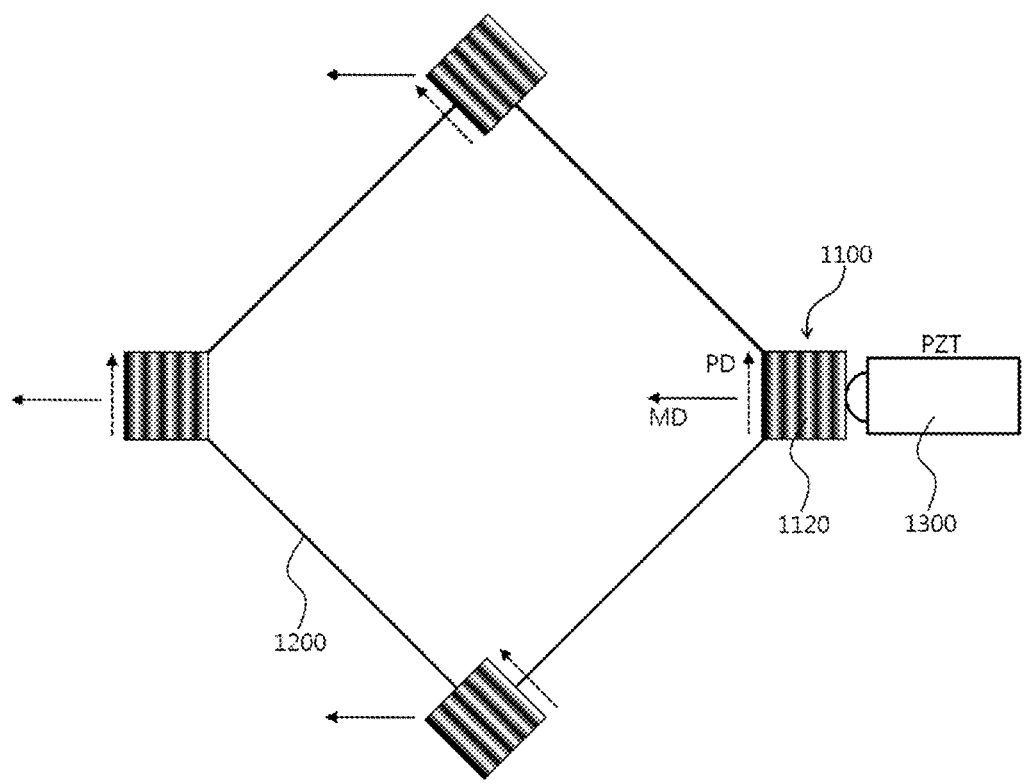
FIG. 9 is a plan view illustrating a board inspection apparatus according to an exemplary embodiment of the present invention.
Figure 10:
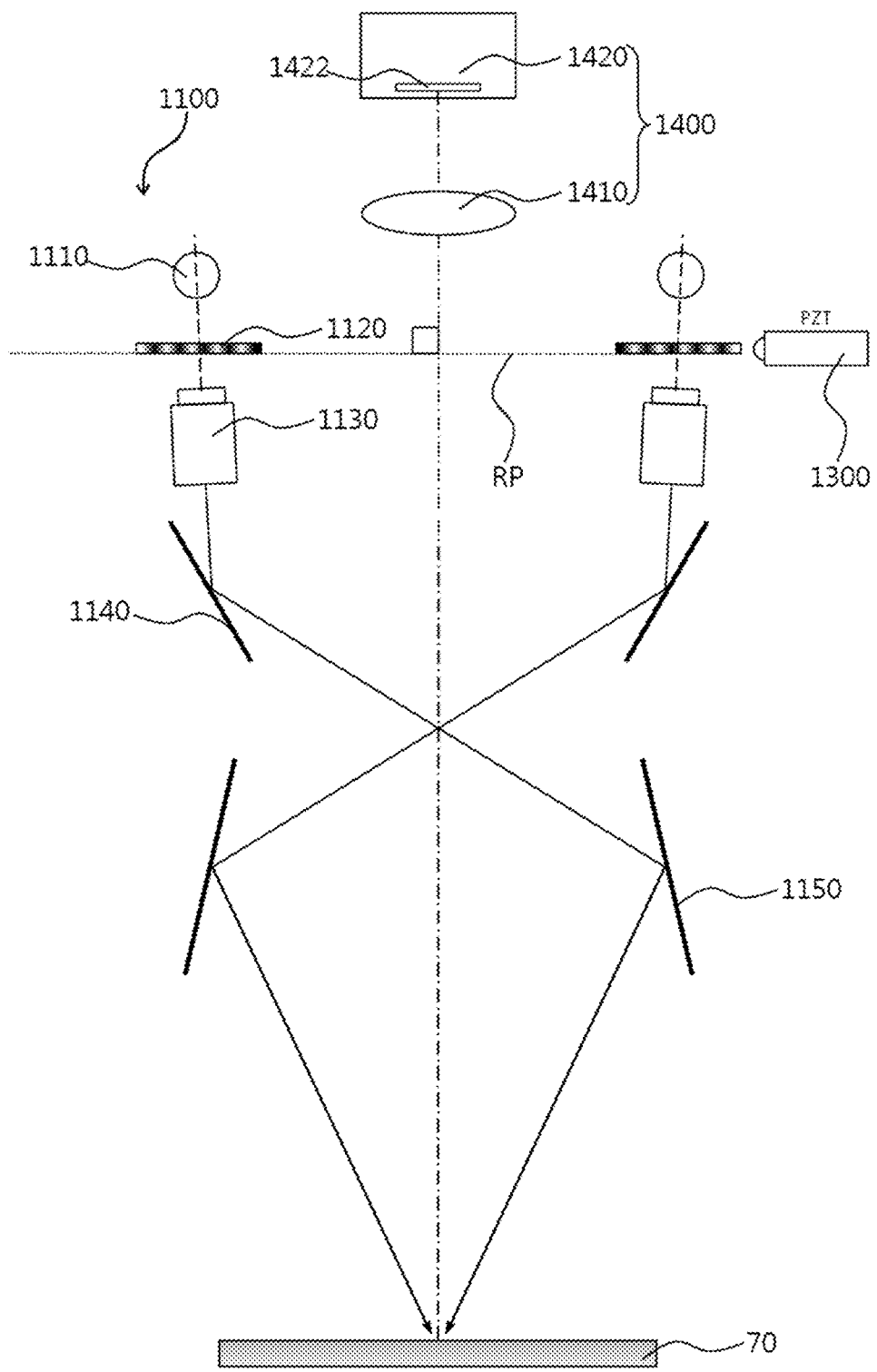
FIG. 10 is a side view illustrating the board inspection apparatus illustrated in FIG. 9.

FIG. 9 is a plan view illustrating a board inspection apparatus according to an exemplary embodiment of the present invention. FIG. 10 is a side view illustrating the board inspection apparatus illustrated in FIG. 9.

Referring to FIGS. 9 and 10, a board inspection apparatus according to an exemplary embodiment of the present invention inspects a three dimensional shape of a surface of an inspection board 70 disposed on a stage (not shown), and the board inspection apparatus includes a plurality of illumination sections 1100, a grating connecting unit 1200, a grating transfer unit 1300, an image photographing module 1400 and a control system (not shown).

Each of the illumination sections 1100 includes a light source unit 1110, a grating unit 1120, a projecting lens 1130 and a light path changing section having a first reflecting minor 1140 and a second reflecting minor 1150. The light source unit 1110 includes a light source and at least one lens to generate a light, and the grating unit 1120 is disposed under the light source unit 1110 to change the light generated by the light source unit 1110 into a grating pattern light having a grating pattern. The projecting lens 1130 is disposed under the grating unit 1120 to pass the grating pattern light exiting the grating unit 1120. The first reflecting minor 1140 reflects the grating pattern light passing through the projecting lens 1130, and the second reflecting mirror 1150 reflects the grating pattern light reflected by the first reflecting mirror 1140 again to provide the reflected grating pattern light to the inspection board 70.

The grating units 1120 are disposed to form substantially the same grating plane RP, and the grating connecting unit 1200 connects the grating units 1120 of the illumination sections 1100 to each other. The grating units 1120 may be disposed at each vertex of a polygon, and for example, may be respectively disposed at four vertices of a square as shown in FIG. 9.

The grating transfer unit 1300 moves the grating units 1120 connected by the grating connecting unit 1200 in a grating transfer direction MD along the grating plane RP. The grating transfer unit 1300 may move the grating units 1120 in the grating transfer direction MD by a predetermined number of times and a selected pitch. The grating transfer unit 1300 may correspond to a piezoelectric (PZT) transfer unit as shown in FIG. 10. Alternatively, the grating transfer unit 1300 may correspond to a fine linear transfer unit. Since grating transfer direction MD moves along the grating plane RP as described above, a distance according to positions of the projecting lens 1130 and the grating unit 1120 is maintained constant, so that magnification is not changed by the transfer of the grating unit 1120.

The grating transfer direction MD is different from grating pattern directions PD of the grating units 1120. In other words, the grating transfer unit 1300 transfers the grating units 1120 in a direction different from the grating pattern directions PD. The grating pattern directions PD may be inclined by about 90 degrees or about 45 degrees with respect to the grating transfer direction MD.

Grating pattern directions of grating units disposed at vertices facing each other of the polygon among the grating units 1120 may be substantially the same. For example, the two grating units facing each other among the grating units respectively disposed at the four vertices of the square may be inclined by about 90 degrees, and another two grating units may be inclined by about 45 degrees.

The image photographing module 1400 receives the grating pattern light that is generated from each of the illumination sections 1100 and reflected by the inspection board 70, and photographs an image. The image photographing module 1400 is disposed a center of the illumination sections 1100, for example, a center of the square.

The image photographing module 1400 includes, for example, an imaging lens 1410 and a camera 1420. The imaging lens 1410 passes the grating pattern light reflected from the inspection board 70 to be provided to the camera. A reference surface of the imaging lens 1410 is substantially in parallel with the grating plane RP, and an optical axis of the imaging lens 1410, which is coincident with a normal line of the reference surface of the imaging lens 1410, is coincident with a normal line of the inspection board 70. The camera 1420 includes a photographing element 1422 that receives the grating pattern light provided from the imaging lens 1410 and photographs an image. For example, the camera 1420 may correspond to one of a CCD camera and a CMOS camera.

The image photographing module 1400 may further include a filter (not shown) and a circular lamp (not shown). The filter is disposed under the imaging lens 1410 to filter the grating pattern light reflected by the inspection board 70 and provide the filtered grating pattern light to the imaging lens 1220. The filter may include, for example, one of a frequency filter, a color filter and a light intensity control filter. The circular lamp is disposed under the filter to provide a light to the inspection board 70, so as to photograph a particular image such as a two dimensional shape of the inspection board 70.

The control system inspects the inspection board 70 by using images photographed by the image photographing module 1400. For example, the control system may further include an image acquiring section, a module control section and a central control section.

The image acquiring section is electrically connected to the camera 1420 to acquire pattern images of the inspection board 70 from the camera 1420 and store the acquired pattern images. The module control section is electrically connected to a stage supporting the inspection board 70, the image photographing module 1400 and the illumination sections 1100, to control the stage supporting the inspection board 70, the image photographing module 1400 and the illumination sections 1100. The module control section may include, for example, an illumination controller controlling the light source units 1110, a grating controller controlling the grating transfer unit 1300 and a stage controller controlling the stage. The central control section is electrically connected to the image acquiring section and the module control section to control the image acquiring section and the module control section. The central control section may include, for example, an image processing board, a control board and an interface board.

Figure 11:
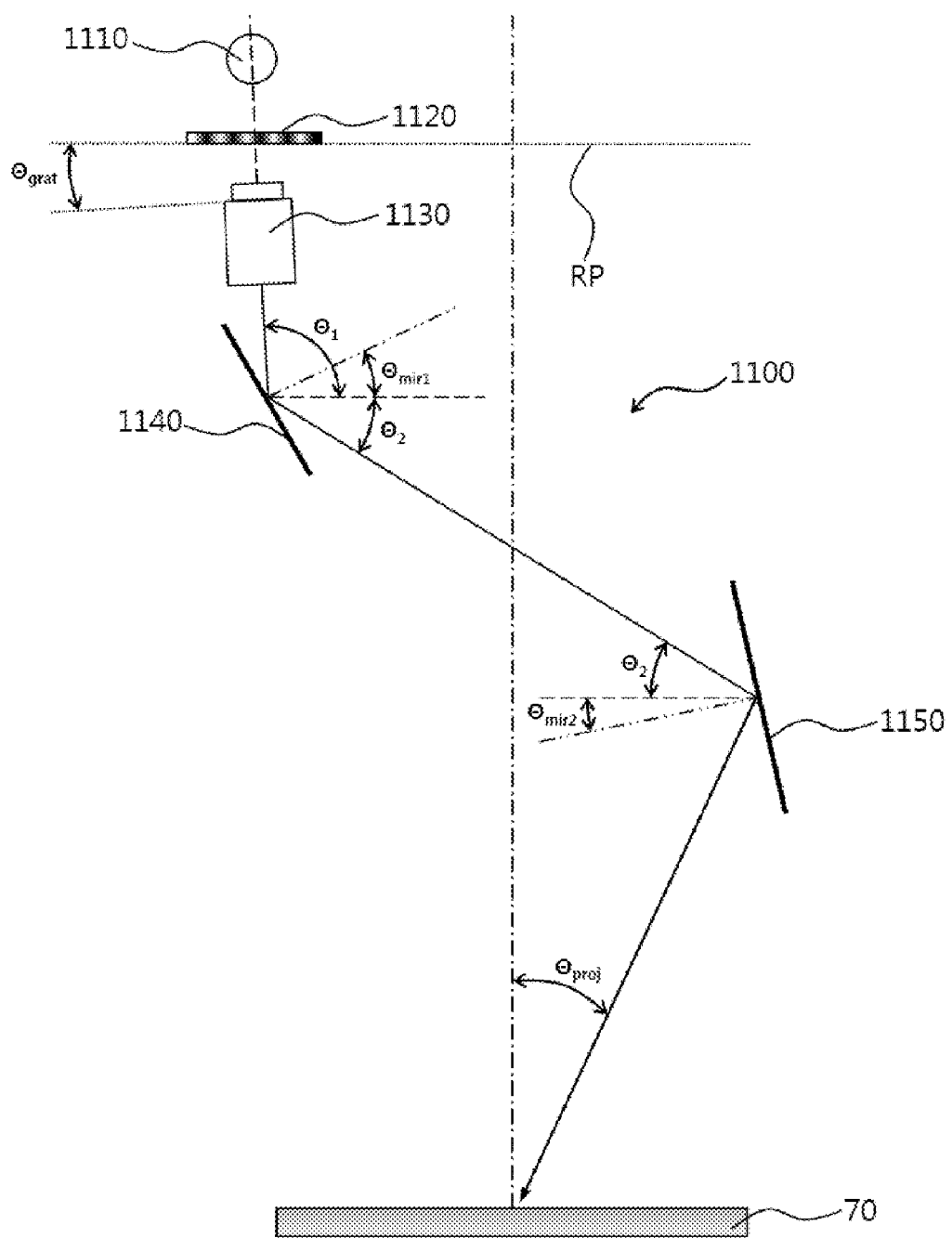
FIG. 11 is a side view illustrating one of illumination sections of the board inspection apparatus illustrated in FIG. 10.

FIG. 11 is a side view illustrating one of illumination sections of the board inspection apparatus illustrated in FIG. 10.

With reference to FIG. 11, one of the illumination sections illustrated in FIGS. 9 and 10 will be described in detail.

First, a reference surface of the projecting lens 1130 is inclined by a predetermined angle with respect to the grating plane RP on which the grating units 1120 are disposed. An angle between the grating plane RP and the reference surface of the projecting lens 1130 is defined as a grating angle θgrat.

A center of a viewing angle of the light generated from the light source unit 1110 is coincident with an optical axis of the projecting lens 1130. The optical axis of the projecting lens 1130 is coincident with a normal line direction of the reference surface of the projecting lens 1130.

Thereafter, the first reflecting mirror 1140 is disposed under the projecting lens 1130 to be inclined by a predetermined angle with respect to the grating plane RP. An angle that is formed by the first reflecting minor 1140 and the grating plane RP, i.e., an angle between a normal line direction of the first reflecting minor 1140 and a horizontal line parallel with the grating plane RP is defined as a first minor angle $\theta mir1$.

Finally, the second reflecting mirror 1150 is disposed under the first reflecting minor 1140 to be inclined by a predetermined angle with respect to the grating plane RP. The first and second reflecting mirrors 1140 and 1150 are disposed at both sides of the optical axis of the imaging lens 1410 of the image photographing module 1400. An angle that is formed by the second reflecting mirror 1150 and the grating plane RP, i.e., an angle between a normal line direction of the second reflecting mirror 1150 and a horizontal line parallel with the grating plane RP is defined as a second minor angle $\theta mir2$. In addition, when the light traveling along the optical axis of the projecting lens 1130 is reflected by the first and second reflecting mirrors 1140 and 1150 and is incident onto the inspection board 70, an angle between the incident light and the normal line of the grating plane RP, i.e. the optical axis of the imaging lens 1410 is defined as a projecting angle $\theta proj$.

Hereinafter, relation between the projecting lens 1410 and the first and second reflecting mirrors 1140 and 1150 will be determined by using the above defined first minor angle $\theta mir1$, the second mirror angle $\theta mir2$, the grating angle $\theta grat$ and the projecting angle $\theta proj$.

First, an angle between the optical axis of the projecting lens 1130 and the horizontal line parallel with the grating plane RP is defined as a first incident angle $\theta 1$. An angle between an incident direction to the second reflecting minor 1150, when the light traveling along the optical axis of the projecting lens 1130 is reflected by the first reflecting minor 1140 and is incident onto the second reflecting mirror 1150, and the horizontal line parallel with the grating plane RP is defined as a second incident angle $\theta 2$. Thus, the following <Equation 1>, <Equation 2> and <Equation 3> may be obtained.

$$\theta 1 = 90 + \theta grat \qquad \text{<Equation 1>}$$

$$\theta 2 = 90 - \theta proj - 2 \cdot \theta mir2 \qquad \text{<Equation 2>}$$

$$\theta 1 - \theta mir1 = \theta mir1 + \theta 2 => \theta 1 = 2 \cdot \theta mir1 + \theta 2 \qquad \text{<Equation 3>}$$

Then, <Equation 2> is applied to <Equation 3> to obtain the following <Equation 4>.

$$\theta 1 = 2 \cdot \theta mir1 + 90 - \theta proj - 2 \cdot \theta mir2 \qquad \text{<Equation 4>}$$

Thereafter, <Equation 4> is applied to <Equation 1> and arranged to obtain the following <Equation 5>.

$$\theta grat + \theta proj = 2 \cdot (\theta mir1 - \theta mir2) \qquad \text{<Equation 5>}$$

Then, <Equation 5> is rearranged to obtain the following <Equation 6>.

$$\theta mir1 - \theta mir2 = (\theta grat + \theta proj)/2 \qquad \text{<Equation 5>}$$

Accordingly, the projecting lens 1410 and the first and second reflecting minors 1140 and 1150 may have the relation of <Equation 6>.

Since the grating angle $\theta grat$ and the projecting angle $\theta proj$ typically have a fixed value, <Equation 6> may be re-expressed as the following <Equation 6-1>.

$$\theta mir1 - \theta mir2 = K \ (K \text{ is a constant}) \qquad \text{<Equation 6-1>}$$

Referring to the above <Equation 6-1>, when the projecting lens 1410 is fixed, the first and second reflecting minors 1140 and 1150 may be disposed so that difference between the first mirror angle $\theta mir1$ and the second minor angle $\theta mir2$ is constant.

Figure 12:
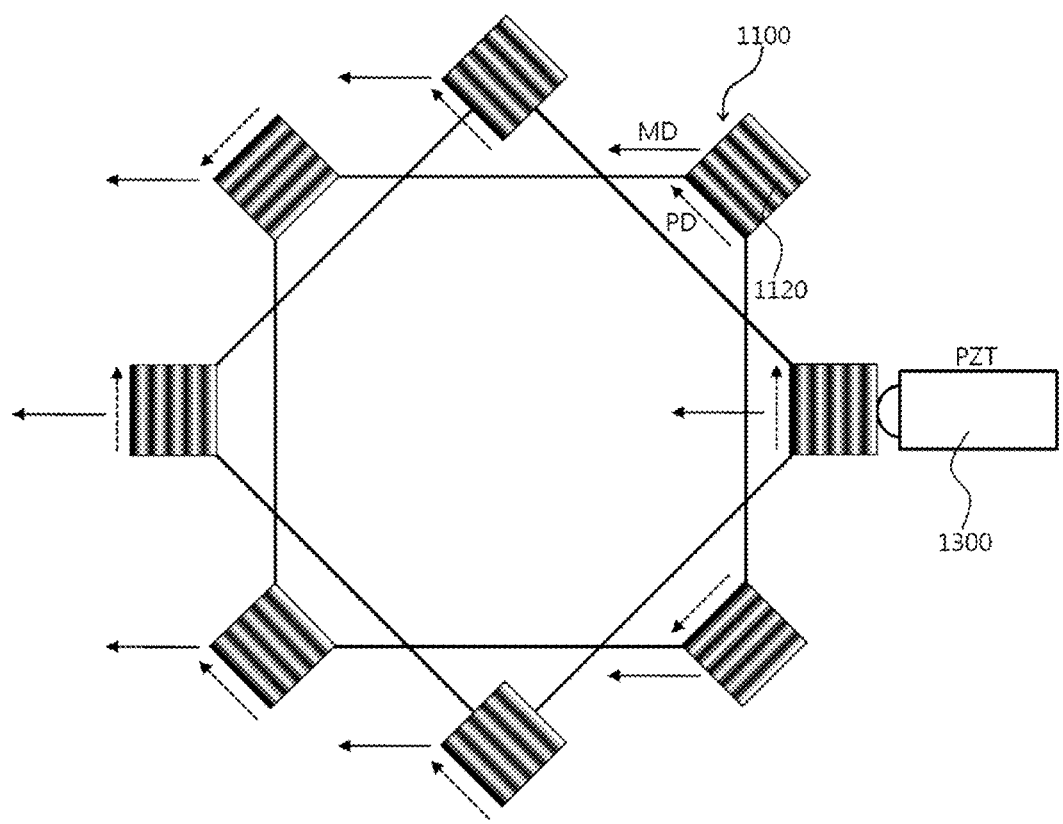
FIG. 12 is a plan view illustrating a board inspection apparatus having the number of illumination sections greater than the number of illumination sections in FIG. 9.

FIG. 12 is a plan view illustrating a board inspection apparatus having the number of illumination sections greater than the number of illumination sections in FIG. 9.

Referring to FIG. 12, in the present embodiment, the number of the illumination is sections 1100 may be increased or decreased. For example, four illumination sections 1100 are newly added to four illumination sections 1100 illustrated in FIG. 9, to respectively dispose the illumination sections 1100 at each vertex of a regular octagon. All of grating pattern directions PD of the newly added four illumination sections 1100 may be inclined by 45 degrees with respect to the grating transfer direction MD illustrated in FIG. 9.

In an exemplary embodiment, the number of the illumination sections 1100, i.e., the number of the grating units 1120 is greater than or equal to three, which is similar to in FIGS. 9 and 12. When the three or more grating units 1120 are controlled by using one grating transfer unit 1300, the grating units 1120 may not be controlled in case that the grating units 1120 are not on the grating plane RP, because no intersected line exists in case that the grating units 1120 are respectively disposed on different grating plane.

Meanwhile, a board inspection method using the above described board inspection apparatus will be described.

First, the grating units 1120 is moved in the grating transfer direction MD along the grating plane RP by a predetermined pitch, by using the grating transfer unit 1300. Then, a light is sequentially provided to the grating units 1120 moved by the predetermined pitch by using the light source units 1110, to provide the grating pattern lights to the inspection board 70. Thereafter, the image photographing module 1400 sequentially photographs images by using the grating pattern lights that is provided to the inspection board 70 and reflected. The above processes are repeatedly performed to acquire image information of the inspection board 70 and inspect a three dimensional shape of a surface of the inspection board 70.

As described above, the grating units 1120 disposed on the same grating plane RP are moved by using one grating transfer unit 1300, to reduce the number of the grating transfer units 1300 and reduce manufacturing cost of the board inspection apparatus, thereby making each illumination section smaller. In addition, reduction of inspection precision due to transfer difference between grating transfer units, which is generated when many conventional grating transfer units are used, may be prevented, and control complexity due to independently operating the grating transfer units may be reduced.

In the present embodiment, each of the illumination sections 1100 includes the light path changing section having the first and second reflecting minors 1140 and 1150. Thus, a photographing available area of the projecting lens 1130 may be used, and the grating pattern light passing through the projecting lens 1130 may be illuminated onto the inspection board 70 together with constantly maintaining a shape thereof.

Figure 13:
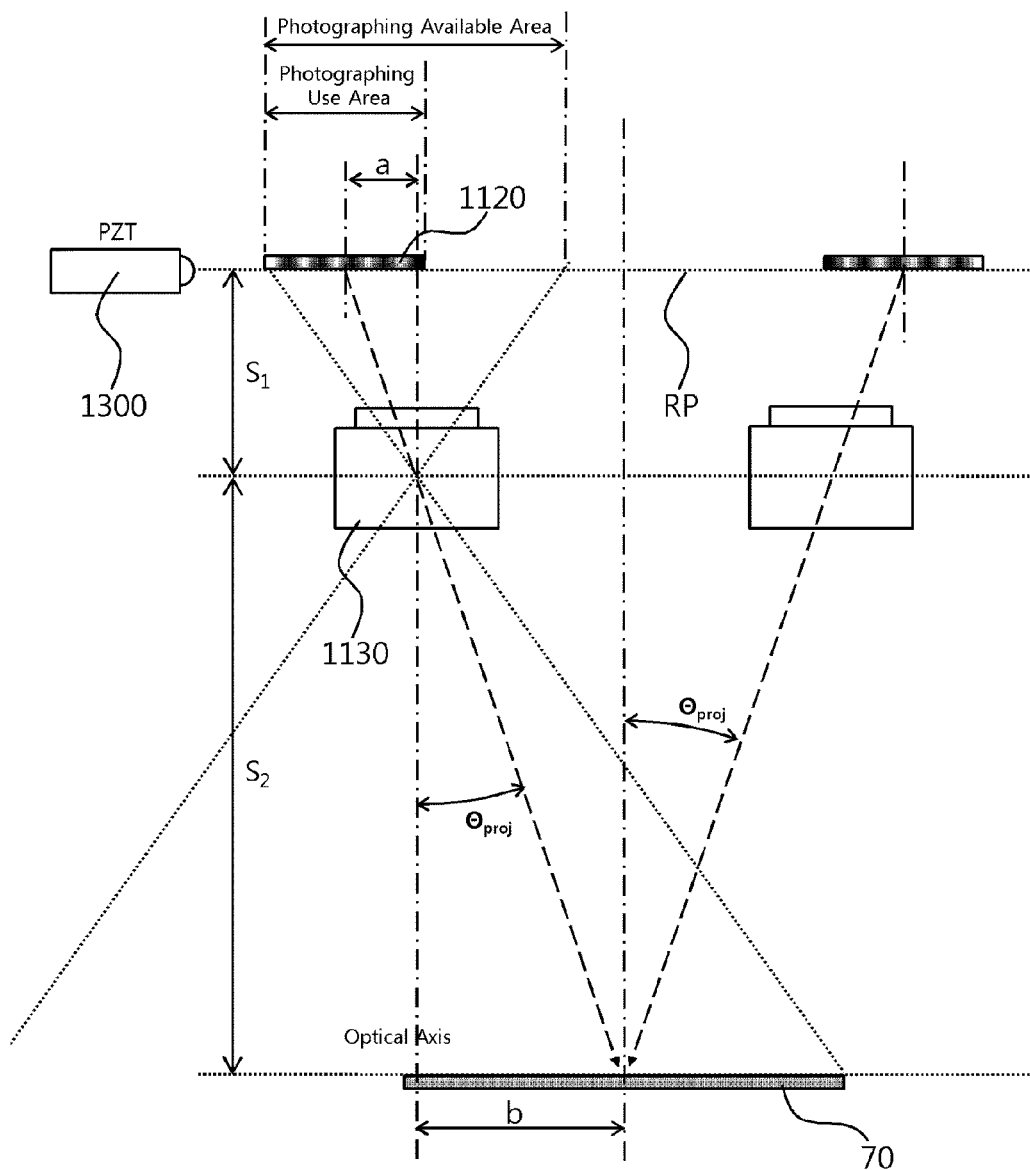
FIG. 13 is a side view illustrating a board inspection apparatus according to another exemplary embodiment of the present invention.

FIG. 13 is a side view illustrating a board inspection apparatus according to another exemplary embodiment of the present invention. The board inspection apparatus illustrated in FIG. 13 is substantially the same as the board inspection apparatus described in FIGS. 9 to 12 except for some features of the illumination sections 1100. Thus, substantially the same elements are referenced by the same reference numeral, and any further description will be omitted.

Referring to FIG. 13, each of illumination sections of the present embodiment does not include the first and second reflecting mirrors 1140 and 1150, which is different from in FIGS. 10 and 11, and includes a light source (not shown), a grating unit 1120 and a projecting lens 1130.

First, a reference surface of the projecting lens 1130 is substantially in parallel with the grating plane RP, which is different from in FIGS. 10 and 11. In other words, an optical axis of the projecting lens 1130 is coincident with a normal line direction of the grating plane RP.

Then, the grating unit 1120 and the projecting lens 1130 are disposed to deviate from each other. In other words, a center of the grating unit 1120 and a center of the projecting lens 1130 are not coincident with each other, but deviate from each other. The center of the projecting lens 1130 is substantially coincident with the optical axis of the projecting lens 1130. In addition, the grating unit 1120 may be disposed to overlap with the center of the projecting lens 1130. As a result, in the projecting lens 1130, a photographing use area, in which real photographing is performed, is included in a photographing available area corresponding to a maximum of an area, in which photographing is possible.

For example, when a center of the inspection board 70 is disposed at a first side of the optical axis of the projecting lens 1130, the grating unit 1120 may be disposed at a second side of the optical axis of the projecting lens 1130 opposite to the first side. In other words, the center of the inspection board 70 is disposed at an inner portion with respect to the optical axes of the projecting lenses 1130, and the grating units 1120 are disposed at an outer portion with respect to the optical axes of the projecting lenses 1130. As a result, each of the projecting lenses 1130 may only use the photographing use area corresponding to one side area of the photographing available area in which both sides with respect to the optical axis are available.

When a distance between the grating plane RP and the reference surface of the projecting lens 1130 is defined as a first interval distance S1, and a distance between the reference surface of the projecting lens 1130 and the inspection board 70 is defined as a second interval distance S2, the following <Equation 7> may be obtained.

$1/S1+1/S2=1/F$ ($F$ is a focus distance of the projecting lens 1130) <Equation 7>

In addition, when a horizontal distance between the optical axis of the projecting lens 1130 and a center of the photographing use area is defined as a photographing middle distance 'a', a horizontal distance between the optical axis of the projecting lens 1130 and the center of the inspection board 70 is defined as an object middle distance 'b', and an angle between the optical axis of the projecting lens 1130 and the normal line of the inspection board 70 is defined as a projecting angle θproj, the following <Equation 8> and <Equation 9> may be obtained by using <Equation 7>.

$a = S1 \cdot \tan \theta_{proj}$ <Equation 8>

$b = S2 \cdot \tan \theta_{proj}$ <Equation 9>

Therefore, each of the illumination sections according to the present embodiment may follows <Equation 8> and <Equation 9>.

As described above, the reference surface of the projecting lens 1130 is disposed substantially parallel with the grating plane RP, and the inspection board 70 and the grating unit 1120 are respectively disposed at both sides with respect to the optical axis of the projecting lens 1130, and thus although the photographing use area is reduced to a portion of the photographing available area, the first and second reflecting mirrors 1140 and 1150 in FIGS. 10 and 11 are omitted, thereby more reducing manufacturing cost of the board inspection apparatus.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A three dimensional shape measurement apparatus comprising:
a first illumination section including a first light source unit generating a light and a first grating unit changing the light generated by the first light source unit into a first grating pattern light having a first grating pattern, the first illumination section illuminating the first grating pattern light onto a measurement target in a first direction;
a second illumination section including a second light source unit generating a light and a second grating unit changing the light generated by the second light source unit into a second grating pattern light having a second grating pattern, the second illumination section illuminating the second grating pattern light onto the measurement target in a second direction different from the first direction; and
a grating transfer unit transferring the first grating unit in a first inclined grating transfer direction that is inclined from an extension direction (y) of the first grating pattern of the first grating unit and an arrangement direction (x) of the first grating pattern of the first grating unit and simultaneously transferring the second grating unit in a second inclined grating transfer direction that is inclined from an extension direction (v) of the second grating pattern of the second grating unit and an arrangement direction (u) of the second grating pattern of the second grating unit,
wherein a plane on which the first grating pattern is disclosed and a plane on which the second grating pattern is disposed are inclined with respect to each other, and an angle between the arrangement direction (x) of the first grating pattern and the first inclined grating transfer direction is θ1, a transfer distance of the first grating unit is 'd' in the first inclined grating transfer direction, and an equivalent grating transfer distance of the first grating unit is d/tan θ1; and an angle between the arrangement direction (u) of the second grating pattern and the second inclined grating transfer direction is θ3, a transfer distance of the second grating unit is 'd' in the second inclined grating transfer direction, and an equivalent grating transfer distance of the second grating unit is d/tan θ3.

2. The three dimensional shape measurement apparatus of claim 1, wherein each of the first and second grating units includes an inclination angle control part controlling an inclination angle of the first and second inclination directions, respectively, and/or the first and second grating units are replaceable to control the inclination angle.

3. The three dimensional shape measurement apparatus of claim 1, wherein the first grating pattern of the first grating unit and the second grating pattern of the second grating unit has a longitudinal direction corresponding to one of a direction substantially in parallel with each other and a direction substantially symmetrical to each other when viewed in a plane view.

4. The three dimensional shape measurement apparatus of claim 1, wherein the first grating pattern light and the second grating pattern light are directly illuminated onto the measurement target.

5. The three dimensional shape measurement apparatus of claim 1, a first equivalent grating transfer direction of the first grating unit and a second equivalent grating transfer direction of the second grating unit are different from the grating transfer direction.

6. A three dimensional shape measurement apparatus as defined in claim 1 wherein:
   θ1 is substantially equal to θ3.

7. A three dimensional shape measurement apparatus as defined in claim 1 wherein:
   θ1 is substantially unequal to θ3.

8. A three dimensional shape measurement apparatus as defined in claim 1 wherein:
   a first illumination section including a first light source unit generating a light and a first grating unit changing the light generated by the first light source unit into a first grating pattern light having a first grating pattern, the first illumination section illuminating the first grating pattern light onto a measurement target in a first direction;
   a second illumination section including a second light source unit generating a light and a second grating unit changing the light generated by the second light source unit into a second grating pattern light having a second grating pattern, the second illumination section illuminating the second grating pattern light onto the measurement target in a second direction different from the first direction;
   a grating transfer unit transferring the first grating unit in a first inclination direction that is inclined from an extension direction of the first grating pattern of the first grating unit and an arrangement direction of the first grating pattern of the first grating unit and simultaneously transferring the second grating unit in a second inclination direction that is substantially parallel with an extension direction of the second grating pattern of the second grating unit and an arrangement direction of the second grating pattern of the second grating unit; and
   wherein a plane on which the first grating pattern is disclosed and a plane on which the second grating pattern is disposed are inclined from each other and an angle between the arrangement direction of the first grating pattern and the grating transfer direction is θ1, and a transfer distance of the first grating unit is "d" and an equivalent grating transfer distance is d/tan θ1 and an angle between the arrangement direction of the second grating pattern and the grating transfer direction is θ3, and a transfer distance of the second grating unit is "d", an equivalent grating transfer distance is d/tan θ1.

9. A three dimensional shape measurement apparatus comprising:
   a first illumination section including a first light source unit generating a light and a first grating unit changing the light generated by the first light source unit into a first grating pattern light having a first grating pattern, the first illumination section illuminating the first grating pattern light onto a measurement target in a first direction;
   a second illumination section including a second light source unit generating a light and a second grating unit changing the light generated by the second light source unit into a second grating pattern light having a second grating pattern, the second illumination section illuminating the second grating pattern light onto the measurement target in a second direction different from the first direction; and
   a grating transfer unit simultaneously transferring the first grating unit changing the light generated by the first light source into the first grating pattern light having the first grating pattern and the second grating unit changing the light generated by the second light source unit into the second grating pattern light having the second grating pattern that are respectively disposed on two inclination faces, which are adjacent to each other and define an edge of an N-angular pyramid, so that the first grating unit and the second grating unit are respectively moved on the two inclination faces.

10. The three dimensional shape measurement apparatus of claim 9, wherein the grating transfer unit moves along the edge defined by the two inclination faces on which the first grating unit and the second grating unit are disposed.

11. A board inspection apparatus comprising:
   a plurality of illumination sections each of which includes a light source unit generating a light, a grating unit changing the light generated by the first light source unit into a grating pattern light, and a projecting lens projecting the grating pattern light;
   a light path changing section providing the grating pattern light passing through the projecting lens to a measurement target;
   a grating transfer unit simultaneously transferring the grating units of the illumination sections by a predetermined number of times;
   an image photographing module photographing images by using the grating pattern lights reflected by the measurement target; and
   a control section inspecting the measurement target by using the photographed images by the photographing module,
   wherein the grating units are disposed on a same plane and simultaneously transferred on the same plane by the grating transfer unit,
   wherein the light path changing section includes:
   a plurality of first reflecting mirrors reflecting the grating pattern light passing through the projecting lens; and
   a plurality of second reflecting mirrors reflecting the grating pattern light reflected by the first reflecting mirror and providing the reflected grating pattern light to the measurement target,
   wherein when an angle between the grating plane and a reference surface of the projecting lens is defined as a grating angle (θgrat), an angle between a normal line of the first reflecting mirror and the grating plane RP is defined as a first mirror angle (θmir1), an angle between a normal line of the second reflecting mirror and the grating plane is defined as a second mirror angle (θmir2), and an angle between an incident light that is reflected by the first and second reflecting mirrors and incident onto the inspection board and the normal line of the grating plane is defined as a projecting angle (θproj), the projecting lens and the first and second reflecting mirrors have a relation of an equation, "$\theta mir1 - \theta mir2 = (\theta grat + \theta proj)/2$".

12. The board inspection apparatus of claim 11, wherein the grating transfer unit simultaneously transfers the grating units in a direction different from grating pattern directions of the grating units.

13. The board inspection apparatus of claim 11, wherein the reference surfaces of the projecting lenses form a predetermined angle with respect to the grating plane.

* * * * *